(12) United States Patent
Derby et al.

(10) Patent No.: US 9,949,925 B2
(45) Date of Patent: Apr. 24, 2018

(54) BACTERICIDAL COMPOSITIONS AND METHODS FOR TREATING PATHOGENIC BIOFILMS (71) Applicant: GEORGIA STATE UNIVERSITY RESEARCH FOUNDATION, Atlanta, GA (US)

(72) Inventors: Charles D. Derby, Decatur, GA (US); Phang C. Tai, Atlanta, GA (US); Eric S. Gilbert, Atlanta, GA (US)

(73) Assignee: GEORGIA STATE UNIVERSITY RESEARCH FOUNDATION, Atlanta, GA (US)

( * ) Notice: Subject to any disclaimer, the term of this patent is extended or adjusted under 35 U.S.C. 154(b) by 0 days.

(21) Appl. No.: 15/089,365

(22) Filed: Apr. 1, 2016

(65) Prior Publication Data

US 2016/0286791 A1 Oct. 6, 2016

Related U.S. Application Data (60) Provisional application No. 62/141,492, filed on Apr. 1, 2015.

(51) Int. Cl.
| | | |
|---|---|---|
| *A61K 9/08* | (2006.01) | |
| *A61K 45/06* | (2006.01) | |
| *A61K 31/195* | (2006.01) | |
| *A61K 31/451* | (2006.01) | |
| *A61K 31/4402* | (2006.01) | |
| *A61K 33/40* | (2006.01) | |
| *A01N 59/00* | (2006.01) | |

(52) U.S. Cl.
CPC ............... *A61K 9/08* (2013.01); *A01N 59/00* (2013.01); *A61K 31/195* (2013.01); *A61K 31/4402* (2013.01); *A61K 31/451* (2013.01); *A61K 33/40* (2013.01); *A61K 45/06* (2013.01)

(58) Field of Classification Search
None
See application file for complete search history.

(56) References Cited

U.S. PATENT DOCUMENTS

2002/0001582 A1* 1/2002 Charter .................... C12G 1/02
424/94.6

OTHER PUBLICATIONS

Aggio et al. Journal of Experimental Marine Biology and Ecology 2008 363:28-34.*
Ko et al. Antimicrobial Agents and Chemotherapy 2008 52(12):4455-4462.*
Christensen et al.(Biofouling 1990 2(2):165-175; online summary version published 2009.*
Vallet et al. Journal of Bacteriology 2004 186(9):2880-2890.*
Biofouling 1990 2(2):165-175.*

* cited by examiner

*Primary Examiner* — Robert A Wax
*Assistant Examiner* — Caralynne E Helm
(74) *Attorney, Agent, or Firm* — Richard S. Echler; FisherBroyles, LLP (57) ABSTRACT Disclosed herein are bactericidal compositions that are effective against pathogenic biofilms, especially against biofilms formed by *Pseudomonas aeruginosa*. The disclosed compositions comprise escapin intermediate products which can reduce the biofilm viability and biofilm matrix of *P. aeruginosa*.

11 Claims, 2 Drawing Sheets

BACTERICIDAL COMPOSITIONS AND METHODS FOR TREATING PATHOGENIC BIOFILMS

CROSS REFERENCE TO RELATED APPLICATIONS

The present Application claims priority to U.S. Provisional Patent Application Ser. No. 62/141,492, filed Apr. 1, 2015, the disclosure of which is included herein by reference in its entirety.

FIELD

Disclosed herein are bactericidal compositions that are effective against pathogenic biofilms, especially against biofilms formed by Pseudomonas aeruginosa. The disclosed compositions comprise escapin intermediate products which can reduce the biofilm viability and biofilm matrix of P. aeruginosa.

BACKGROUND

Biofilms are microbial communities encased in a matrix of extracellular polymeric substance composed of extracellular DNA, proteins, lipids, and polysaccharides which adhere to and grow on biotic and abiotic surfaces. Biofilm formation is a genetically controlled process in the life cycle of bacteria that produces numerous changes in the cellular physiology of the organism, often including increased antibiotic resistance (of up to 100 to 1000 times), as compared to growth under planktonic (free floating) conditions. Diverse microorganisms form biofilms in response to environmental stress, nutritional starvation, oxygen depletion, or exposure to chemicals including antibiotics. Biofilms begin to form when cells attach to the substratum, form a monolayer then proliferate to form microcolonies and extensive networks of extracellular polymeric substances. The microcolony matures into a more complex three dimensional structure of biofilm.

As the organisms grow, problems with overcrowding and diminishing nutrition trigger shedding of the organisms to seek new locations and resources. The newly shed organisms quickly revert back to their original free-floating phase and are once again vulnerable to antibiotics. Free-floating organisms, however, in the context of site infections such as wounds, surgical sites and burns, can enter the bloodstream of a patient, creating bloodstream infections and serious infection-related consequences. Sessile rafts of biofilm may slough off and may attach to tissue surfaces, such as heart valves, causing proliferation of biofilm and serious problems, such as endocarditis.

As such, biofilms have profound health and environmental implications. Biofilms on medical devices such as catheters or implants can result in chronic infections that are resistant to therapeutic drugs. Moreover, nosocomial infections have been associated with biofilm formation on human surfaces such as teeth, skin, and urinary tract.

Biofilms are more resistant to antimicrobial agents such as antibiotics than are their planktonic counterparts. Moreover, biofilms contain persister cells that neither grow nor die in the presence of antimicrobial agents, and thus confer on them multidrug resistance. This resistance can result from the thickness of the biofilm matrix preventing penetration of antimicrobials through the biofilm, resulting in cells in the biofilm being protected from external treatment. Additionally, bacteria living in biofilms adopt an altered metabolic state, including increasing extracellular enzymatic activity inside the biofilms which confers on them more resistance to antimicrobials. Extracellular polymeric substances may form barriers or make complexes with the antimicrobials, thus preventing or reducing the antimicrobial action. Moreover, biofilms can generate different microenvironments within their layers with altered levels of $CO_2$, oxygen, cations, pH, and other variables, which may affect the activity of antimicrobials. For these reasons, biofilms represent an important challenge for public health, necessitating the development of novel antimicrobial and therapeutic agents.

DETAILED DISCLOSURE

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

A weight percent of a component, unless specifically stated to the contrary, is based on the total weight of the composition in which the component is included.

By "effective amount" as used herein means "an amount of the disclosed escapin intermediate products, effective at dosages and for periods of time necessary to achieve the desired result."

Throughout the description and claims of this specification, the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise.

"Optional" or "optionally" means that the subsequently described event or circumstance can or cannot occur, and that the description includes instances where the event or circumstance occurs and instances where it does not.

The antecedent "about" indicates that the values are approximate. The range of "about 1 μM to about 50 μM" includes approximate and specific values, e.g., the range includes about 1 μM, 1 μM, about 50 μM and 50 μM.

The terms such as "comprises", "comprised", "comprising", "contains", "containing" and the like have the meaning attributed in U.S. Patent law; these terms are inclusive or open-ended and do not exclude additional, unrecited elements or method steps. Terms such as "consisting essentially of" and "consists essentially of" have the meaning attributed to them in U.S. Patent law; these terms allow for the inclusion of additional ingredients or steps that do not materially affect the basic and novel characteristics of the claim invention. The terms "consists of" and "consisting of" have the meaning ascribed to them in U.S. Patent law; these terms are close ended.

When a range is described, the range includes both the endpoints of the range as well as all numbers in between. For example, "between 1 μM and 10 μM" includes 1 μM, 10 μM and all amounts between 1 μM and 10 μM. Likewise, "from 1 μM to 10 μM" includes 1 μM, 10 μM and all amounts between 1 μM and 10 μM.

Disclosed herein are bactericidal compositions effective for treating biofilms formed by, or otherwise comprising, *Pseudomonas aeruginosa*, said compositions comprising:

a) an effective amount of one or more escapin intermediate products (EIP); and
b) a source of hydrogen peroxide.

The "one or more escapin intermediate products" are also referred to herein as the "antimicrobial component." It has been found that a mixture of compounds formed in situ as a result of a defense mechanism of the sea snail, *Aplysia californica*, can be used as an antimicrobial component in compositions useful in treating bacterial biofilms. See, for example, Kamio M. et al. "The Chemistry of Escapin: Identification and Quantification of the Components in the Complex Mixture Generated by an L-Amino Acid Oxidase in the Defensive Secretion of the Sea Snail *Aplysia californica*," Chem. Eur. J. 2009, 15, 1597-1603 which is included herein by reference in its entirety.

The escapin intermediate products mixture can be formed by preparing an aqueous solution of the compound $\Delta^1$-piperideine-2-carboxylic acid having the formula (1):

This compound in solution undergoes as series of equilibria as indicated in Scheme I below:

(3)

Depending upon the pH of the solution, the equilibrium can be shifted in a manner that favors one or more species. For example, at lower pH compounds (2) (α-keto-ε-aminocaproic acid), (4) (2-hydroxypiperidine-2-carboxylic acid) and (5) (6-amino-2-hydroxyhex-2-enoic acid) are favored, while compound (3) ($\Delta^1$-piperideine-2-carboxylic acid) is favored at higher pH. Compound (1), however, is the major component of the equilibria at all pH values.

For the purposes of the present disclosure the term "$\Delta^1$-piperideine-2-carboxylic acid and the equilibrium products thereof" is defined as the compounds that are formed in solution when $\Delta^1$-piperideine-2-carboxylic acid is dissolved in an aqueous based carrier. Although, as described herein, the relative amounts of the compounds in the equilibrium mixture are dependent upon pH of the solution, the source of the products derives from $\Delta^1$-piperideine-2-carboxylic acid."

As stated herein above, the disclosed compositions further comprise a source of hydrogen peroxide. The addition of hydrogen peroxide introduces several irreversible transformations which are also dependent on the pH of the composition. These products of these irreversible reactions are the result of the equilibrium components reacting with hydrogen peroxide to convert escapin intermediate products (EIP) to escapin end products (EEP), compounds (7) and (8), as depicted in Scheme II herein below.

Scheme II

For the purposes of the present disclosure a composition comprising $\Delta^1$-piperideine-2-carboxylic acid is defined herein as a composition that comprises $\Delta^1$-piperideine-2-carboxylic acid and all equilibrium species as described in Schemes I and II. For example, a composition comprising about 10 μM of $\Delta^1$-piperideine-2-carboxylic acid, comprises all compounds 1 to 6 as described herein above such that the sum total concentration of these compounds is about 10 μM. Likewise, for compositions wherein a source of hydrogen peroxide has been added, the composition can comprise all of the compounds 1 to 8 as described herein above such that the sum total concentration of these compounds is about 10 μM.

COMPOSITIONS

As stated hereinabove, disclosed are bactericidal compositions effective for treating biofilms formed by, or otherwise comprising, *Pseudomonas aeruginosa*, said compositions comprising:
 a) an effective amount of one or more escapin intermediate products (EIP); and
 b) a source of hydrogen peroxide.

Dissolving $\Delta^1$-piperideine-2-carboxylic acid in water or other aqueous carrier will result in the equilibria disclosed in Schemes I and II, however, the relative amounts of each intermediate, or lack thereof, will be affected by the pH of the composition. The present disclosure relates to compositions which are pre-formulated and to compositions which are prepared at the time of use.

The amount of hydrogen peroxide necessary to affect the bactericidal activity of the disclosed compositions is far below the amount that is necessary for achieving bactericidal activity using hydrogen peroxide alone.

In one aspect the present disclosure relates to pre-formulated antimicrobial compositions that are effective for treating biofilms that comprise *Pseudomonas aeruginosa*, the compositions comprising:
 a) $\Delta^1$-piperideine-2-carboxylic acid; and
 b) hydrogen peroxide.

Stated another way, the compositions comprise:
 a) escapin intermediate products (EIP) as defined herein; and
 b) hydrogen peroxide.

Therefore, compositions which are indicated to comprise, for example, 50 μM of $\Delta^1$-piperideine-2-carboxylic acid will comprise 50 μM of the total mass of the escapin intermediate products. Stated another way, if 1 gram of $\Delta^1$-piperideine-2-carboxylic acid is dissolved in water, the total weight of the equilibrium products will be approximately 1 gram. As such, a composition comprising 50 μM of $\Delta^1$-piperideine-2-carboxylic acid is the same as a composition comprising 50 μM of escapin intermediate products.

In one embodiment of this aspect, the composition comprises:
 a) $\Delta^1$-piperideine-2-carboxylic acid;
 b) hydrogen peroxide; and
 c) an aqueous carrier.

In one iteration of this aspect, the composition comprises:
 a) from about 5 micromolar (μM) to about 500 μM of $\Delta^1$-piperideine-2-carboxylic acid;
 b) from about 0.0001 μM to about 100 μM of hydrogen peroxide; and
 c) the balance water.

The following are non-limiting examples of this iteration.

An antimicrobial composition, comprising:
 a) about 50 μM of $\Delta^1$-piperideine-2-carboxylic acid;
 b) from about 0.03 μM to about 30 μM of hydrogen peroxide; and
 c) the balance water.

An antimicrobial composition, comprising:
 a) from about 30 μM to about 70 μM of $\Delta^1$-piperideine-2-carboxylic acid;
 b) about 0.3 μM of hydrogen peroxide; and
 c) the balance water.

An antimicrobial composition, comprising:
 a) from about 30 μM to about 70 μM of $\Delta^1$-piperideine-2-carboxylic acid;
 b) about 3 μM of hydrogen peroxide; and
 c) the balance water.

An antimicrobial composition, comprising:
 a) from about 30 μM to about 70 μM of $\Delta^1$-piperideine-2-carboxylic acid;
 b) about 30 μM of hydrogen peroxide; and
 c) the balance water.

An antimicrobial composition, comprising:
 a) from about 30 μM to about 70 μM of $\Delta^1$-piperideine-2-carboxylic acid;
 b) about 100 μM of hydrogen peroxide; and
 c) the balance water.

An antimicrobial composition, comprising:
 a) from about 30 μM to about 70 μM of $\Delta^1$-piperideine-2-carboxylic acid;
 b) about 50 μM of hydrogen peroxide; and
 c) the balance water.

Table 1 depicts non-limiting examples of the disclosed pre-formulated bactericidal compositions.

TABLE 1

| Ex. | EIP (μM) | $H_2O_2$ (nM) |
| --- | --- | --- |
| 1 | 50 | 0.03 |
| 2 | 50 | 0.04 |
| 3 | 50 | 0.05 |
| 4 | 50 | 0.06 |
| 5 | 50 | 0.07 |
| 6 | 50 | 0.08 |
| 7 | 50 | 0.09 |
| 8 | 50 | 0.1 |
| 9 | 50 | 0.11 |
| 10 | 50 | 0.12 |
| 11 | 50 | 0.13 |
| 12 | 50 | 0.14 |
| 13 | 50 | 0.15 |
| 14 | 50 | 0.16 |
| 15 | 50 | 0.17 |
| 16 | 50 | 0.18 |
| 17 | 50 | 0.19 |
| 18 | 50 | 0.2 |
| 19 | 50 | 0.21 |
| 20 | 50 | 0.22 |
| 21 | 50 | 0.23 |
| 22 | 50 | 0.24 |
| 23 | 50 | 0.3 |
| 24 | 50 | 0.31 |
| 25 | 50 | 0.32 |
| 26 | 50 | 0.33 |
| 27 | 50 | 0.34 |
| 28 | 50 | 0.35 |
| 29 | 50 | 0.36 |
| 30 | 50 | 0.37 |
| 31 | 50 | 0.38 |
| 32 | 50 | 0.39 |
| 33 | 50 | 0.4 |
| 34 | 50 | 0.41 |
| 35 | 50 | 0.42 |
| 36 | 50 | 0.43 |

TABLE 1-continued

| Ex. | EIP (µM) | H$_2$O$_2$ (nM) |
|---|---|---|
| 37 | 50 | 0.44 |
| 38 | 50 | 0.45 |
| 39 | 50 | 0.46 |
| 40 | 50 | 0.47 |
| 41 | 50 | 0.48 |
| 42 | 50 | 0.49 |
| 43 | 50 | 0.5 |
| 44 | 50 | 0.51 |
| 45 | 50 | 0.52 |
| 46 | 50 | 0.53 |
| 47 | 50 | 0.54 |
| 48 | 50 | 0.55 |
| 49 | 50 | 0.56 |
| 50 | 50 | 0.57 |
| 51 | 100 | 1 |
| 52 | 100 | 1.1 |
| 53 | 100 | 1.2 |
| 54 | 100 | 1.3 |
| 55 | 100 | 1.4 |
| 56 | 100 | 1.5 |
| 57 | 100 | 1.6 |
| 58 | 100 | 1.7 |
| 59 | 100 | 1.8 |
| 60 | 100 | 1.9 |
| 61 | 100 | 2 |
| 62 | 100 | 2.1 |
| 63 | 100 | 2.2 |
| 64 | 100 | 2.3 |
| 65 | 100 | 2.4 |
| 66 | 100 | 2.5 |
| 67 | 100 | 2.6 |
| 68 | 100 | 2.7 |
| 69 | 100 | 2.8 |
| 70 | 100 | 2.9 |
| 71 | 100 | 3 |
| 72 | 100 | 3.1 |
| 73 | 100 | 3.2 |
| 74 | 100 | 3.3 |
| 75 | 100 | 3.4 |
| 76 | 100 | 3.5 |
| 77 | 100 | 3.6 |
| 78 | 100 | 3.7 |
| 79 | 100 | 3.8 |
| 80 | 100 | 3.9 |
| 81 | 100 | 4 |
| 82 | 100 | 4.1 |
| 83 | 100 | 4.2 |
| 84 | 100 | 4.3 |
| 85 | 100 | 4.4 |
| 86 | 100 | 4.5 |
| 87 | 100 | 4.6 |
| 88 | 100 | 4.7 |
| 89 | 100 | 4.8 |
| 90 | 100 | 4.9 |
| 91 | 100 | 5 |
| 92 | 100 | 5.1 |
| 93 | 100 | 5.2 |
| 94 | 100 | 5.3 |
| 95 | 100 | 5.4 |
| 96 | 100 | 5.5 |
| 97 | 100 | 5.6 |
| 98 | 100 | 5.7 |
| 99 | 100 | 5.8 |
| 100 | 100 | 5.9 |
| 101 | 250 | 10 |
| 102 | 250 | 10.5 |
| 103 | 250 | 11 |
| 104 | 250 | 11.5 |
| 105 | 250 | 12 |
| 106 | 250 | 12.5 |
| 107 | 250 | 13 |
| 108 | 250 | 13.5 |
| 109 | 250 | 14 |
| 110 | 250 | 14.5 |
| 111 | 250 | 15 |
| 112 | 250 | 15.5 |
| 113 | 250 | 16 |
| 114 | 250 | 16.5 |
| 115 | 250 | 17 |
| 116 | 250 | 17.5 |
| 117 | 250 | 18 |
| 118 | 250 | 18.5 |
| 119 | 250 | 19 |
| 120 | 250 | 19.5 |
| 121 | 250 | 20 |
| 122 | 250 | 20.5 |
| 123 | 250 | 21.5 |
| 124 | 250 | 22 |
| 125 | 250 | 22.5 |
| 126 | 250 | 23 |
| 127 | 250 | 23.5 |
| 128 | 250 | 24 |
| 129 | 250 | 24.5 |
| 130 | 250 | 25 |
| 131 | 250 | 25.5 |
| 132 | 250 | 26 |
| 133 | 250 | 26.5 |
| 134 | 250 | 27 |
| 135 | 250 | 27.5 |
| 136 | 250 | 28 |
| 137 | 250 | 28.5 |
| 138 | 250 | 29 |
| 139 | 250 | 29.5 |
| 140 | 250 | 30 |
| 141 | 250 | 30.5 |
| 142 | 250 | 31 |
| 143 | 250 | 31.5 |
| 144 | 250 | 32 |
| 145 | 250 | 32.5 |
| 146 | 250 | 33 |
| 147 | 250 | 33.5 |
| 148 | 250 | 34 |
| 149 | 250 | 34.5 |
| 150 | 250 | 35 |

Further disclosed herein are compositions which are prepared or formulated by the user prior to applying the composition to a situs; for example, a medical professional who is applying the composition to a wound or other potential site of infection. Other examples of users who can reconstitute the compositions include workers sanitizing surfaces. Kits for re-formulation can further comprise instructions that allow for the user to modify or choose the relative concentration of the escapin intermediate products and/or the amount of hydrogen peroxide.

In one iteration of this aspect, the composition comprises:
a) from about 5 micromolar (µM) to about 500 µM of $\Delta^1$-piperideine-2-carboxylic acid;
b) from about 0.0001 µM to about 100 µM of hydrogen peroxide; and
c) the balance water.

The water can be delivered as part of a 3% solution of hydrogen peroxide. For example, a 3% w/w solution of hydrogen peroxide is approximately 1.27 M in H$_2$O$_2$.

To a 1 L volumetric flask containing 750 mL of distilled water is charged $\Delta^1$-piperideine-2-carboxylic acid (6.4 mg, 50 µmol) and the solution is shaken to dissolve the solids. A 0.03% solution of hydrogen peroxide (2.3 µL) is added and the solution is diluted to 1 liter.

Buffer System

The disclosed compositions have a pH of from about 3 to about 8. In one embodiment the pH is from about 5 to about 7. In another embodiment, the pH is from about 5 to about 6. In a further embodiment, the pH is from about 4.5 to about 5.5. In a further embodiment, the pH is about 5. In a still further embodiment, the pH is about 6. The compositions, however, can have any pH from about 3 to about 8 or any fractional part thereof, for example, a pH of 3, 3.5, 4, 4.5, 5, 5.5, 6, 6.5, 7, 7.5, and 8.

The disclosed compositions can comprise a buffer system to maintain the pH of the compositions whether pre-formulated as a liquid, diluted at the time of use, or whether constituted at the time of use, at a pH of from about 3 to about 8. In one embodiment the pH is from about 5 to about 7. In another embodiment, the pH is from about 5 to about 6. In a further embodiment, the pH is from about 4.5 to about 5.5. In a further embodiment, the pH is about 5. In a still further embodiment, the pH is about 6. The compositions, however, can comprise a buffer system to buffer the pH from about 3 to about 8 or any fractional part thereof, for example, a pH of 3, 3.5, 4, 4.5, 5, 5.5, 6, 6.5, 7, 7.5, and 8.

The formulator, depending upon the level of antimicrobial activity desired, can adjust the pH of the solution to be compatible with the type of microorganism being treated or the situs of application, for example, the skin of a burn victim, an open wound, an inert surface, or a food surface.

Noon-limiting examples of suitable organic acid buffer systems include acetic acid/sodium acetate, glycolic acid/sodium glycolate, lactic acid/sodium lactate, succinic acid/mono sodium succinate, adipic acid/mono sodium adipate, malic acid/mono sodium malate, tartaric acid/mono sodium tartrate, and the like. Non-limiting examples of suitable inorganic buffer systems include phosphate buffer systems.

Because the source of oxidizer, for example, hydrogen peroxide in the disclosed compositions are susceptible to degradation in the presence of metals, the compositions can comprise one or more compatible metal chelants. Organic acids, for example, citric acid can be used as a metal chelant. The use of organic acids can have the added benefit as acting as a part of a buffer system to regulate the pH of the activator composition. Non-limiting examples of organic acids includes malonic acid, succinic acid, adipic acid fumaric acid, malic acid, maleic acid, citric acid, ethylenediamine tertraacetic acid, N-(hydroxyethyl)-ethylenediaminetriacetic acid, and the like.

METHODS

Disclosed herein are methods for treating *P. aeruginosa* biofilms or biofilms comprising *P. aeruginosa*. One aspect of the disclosed methods relates to contacting *P. aeruginosa* biofilms, comprising contacting the biofilm with a bactericidal composition as described herein, for example, a composition comprising:
   a) an effective amount of one or more escapin intermediate products (EIP); and
   b) a source of hydrogen peroxide.

Another aspect relates to a method for treating *P. aeruginosa* biofilms with a composition that is prepared at the time of use. For example, a method for treating a *P. aeruginosa* biofilm, comprising:
   A) preparing an aqueous solution of $\Delta^1$-piperideine-2-carboxylic acid;
   B) admixing the aqueous solution of step (A) with a source of hydrogen peroxide to form a composition, comprising:
      a) from about 5 µM to about 500 µM of $\Delta^1$-piperideine-2-carboxylic acid;
      b) from about 0.0001 µM to about 100 µM of hydrogen peroxide; and
      c) the balance water; and
   C) contacting a *P. aeruginosa* biofilm with the composition formed in step (B).

One aspect of the disclosed methods relates to the treatment of human skin infections. As such, disclosed herein is a method for treating human skin infections, comprising contacting a subject having an infection caused by a pathogen. In one embodiment, the pathogen is *P. aeruginosa*.

Disclosed is a method for treating a skin infection or wound wherein *P. aeruginosa* is present, comprising contacting the infection or wound with a composition comprising:
   a) from about 30 µM to about 70 µM of the disclosed escapin intermediate products;
   b) from about 1 µM to about 150 µM of hydrogen peroxide; and
   c) a liquid carrier.

One iteration of this method relates to contacting a skin infection or wound wherein *P. aeruginosa* is present, comprising contacting the infection or wound with a composition comprising:
   a) about 50 µM of the disclosed escapin intermediate products;
   b) about 3 µM of hydrogen peroxide; and
   c) water.

Another iteration, the compositions comprise:
   a) about 50 µM of the disclosed escapin intermediate products;
   b) about 100 µM of hydrogen peroxide; and
   c) water.

Compositions according to this iteration can be conveniently used to treat larger or deeper wounds. One advantage of the present methods relates to the fact that wounds have a naturally occurring amount of hydrogen peroxide. In cases wherein the level of hydrogen peroxide is naturally elevated, the formulator can adjust the amount of the composition applied to a wound or modify the amount of hydrogen peroxide. As described herein above, the user can prepare the formulation prior to use and at that time adjust the amount of hydrogen peroxide in the formulation.

The compositions for treating a wound or infection can be applied at the time the infection is first treated and at any time subsequent to the first treatments. The volume of the composition applied can vary depending upon the extent of the wound or infection. The compositions can be administered alone or in combination with other wound or infection treatments, for example, other antibacterial agents, dressings or skin treatment agents.

A further aspect of the disclosed methods relates to cleaning hard surfaces wherein a biofilm comprising *P. aeruginosa* is present. As such, disclosed are methods for treating a surface wherein *P. aeruginosa* is present. The method comprising contacting the surface with a composition comprising:
   a) from about 30 µM to about 70 µM of the disclosed escapin intermediate products;
   b) from about 50 µM to about 150 µM of hydrogen peroxide; and
   c) a liquid carrier.

One iteration of this method relates to contacting a surface wherein *P. aeruginosa* is present, comprising contacting the surface with a composition comprising:
   a) about 50 µM of the disclosed escapin intermediate products;
   b) about 100 µM of hydrogen peroxide; and
   c) water.

Another iteration, the compositions comprise:
   a) about 70 µM of the disclosed escapin intermediate products;
   b) about 150 µM of hydrogen peroxide; and
   c) water.

In a further aspect of the disclosed methods the surfaces to be treated are any surfaces which comprise a biofilm formed by a pathogen, especially a bacterial biofilm. As such, the present disclosure also relates to compositions for treating a surface that can have any biofilm present. Disclosed are methods for treating a surface having a biofilm that is formed by a pathogen, the composition comprising:
a) from about 30 μM to about 150 μM of the disclosed escapin intermediate products;
b) from about 10 μM to about 300 μM of hydrogen peroxide; and
c) a liquid carrier.

PROCEDURES $\Delta^1$-Piperideine-2-carboxylic acid was synthesized as described in Kamio (see, Kamio M. et al. "The Chemistry of Escapin: Identification and Quantification of the Components in the Complex Mixture Generated by an L-Amino Acid oxidase in the Defensive Secretion of the Sea Snail *Aplysia californica,*" *Chem. Eur. J.* 2009, 15, 1597-1603) which is included herein by reference in its entirety, which is in turn based on the procedure of Lu (Lu, S. P. et al., *Tetrahedron* 1998, 54, 15097-15104) the entirety of which is included herein by reference. This is a non-enzymatic synthesis starting with pipecolinic acid ethyl ester. In that synthesis $\Delta^1$-piperideine-2-carboxylic acid (1) is the major product whereas the isomer, $\Delta^1$-piperideine-2-carboxylic acid (3), is formed in minor amounts. Solutions of $\Delta^1$-piperideine-2-carboxylic acid yielding the escapin intermediate products (EIP) were prepared from a 1 M (w/v) stock solution stored at −80° C. Hydrogen peroxide (Sigma-Aldrich) solutions were prepared from 30% (w/w) stock solution and stored at 4° C. On each day of use, solutions of EIP and $H_2O_2$ were prepared by serial dilution using a sterile 50 mM KCl/NaCl solution (pH 7.0).

Cultures and Media

*Pseudomonas aeruginosa* strain PAO1 was used for the disclosed examples. The *P. aeruginosa* was stored as a frozen stock in 20% glycerol at −80° C. Cultures were grown on Luria Bertani (LB) agar on plates incubated at 37° C. for 16-18 hours. To produce biofilms, the overnight culture was diluted to OD600 of 0.01 in *Pseudomonas* basal mineral media (PBM), which comprises the following in a total volume of 1 liter:

TABLE 2

| Ingredient | Mass (g) |
|---|---|
| $K_2HPO_4$ | 12.5 |
| $KH_2PO_4$ | 3.8 |
| $(NH_4)_2SO_4$ | 1.0 |
| $MgSO_4 \cdot 7H_2O$ | 0.1 |
| glucose | 144 |
| water | balance |
| pH | 7.2 |

Assessment

Biofilms were cultivated in flow cells as described elsewhere (Gilbert and Keaslin, 2004; Niu and Gilbert, 2004; Pittman et al., 2010) except with PBM as growth medium.

After growing biofilms in flow cells for 24 hours, they were rinsed with a sterile 50 mM KCl—NaCl solution (pH 7.0) for 20 min. After rinsing, control solutions (saline), compositions comprising $\Delta^1$-piperideine-2-carboxylic acid (escapin intermediate products, EIP), EIP and hydrogen peroxide, and hydrogen peroxide were pumped for 30 minutes through the flow cells, and then the biofilms were rinsed for 10 minutes. To assess cell viability of biofilms, each flow cell received 1 mL of a 1:1,000-diluted LIVE/DEAD™ Baclight™ nucleic acid stain (SYTO 9, 3.34 mM; propidium iodide, 20 mM) for 15 minutes, followed by rinsing with 50 mM KCl/NaCl solution for another 5 minutes, and then examined using Zeiss LSM 510 confocal laser scanning microscope. Argon and helium lasers were used with excitation/emission wavelengths of 480/500 nm for SYTO 9 and 490/635 nm for propidium iodide. Long-pass and dual emission filters were used for simultaneous viewing of SYTO 9 and propidium iodide stains. SYTO 9 is a green fluorescent label of nucleic acids that is permeant to cell membranes of normal cells and is thus used to label live and undamaged cells. Propidium iodide is a red-fluorescent label of nucleic acids, and since the intact cell membranes of live and undamaged cells are not normally permeant to propidium iodide, propidium iodide is used to detect cells that are dead or with damaged membranes. At least four image stacks were collected from each biofilm and at least three independent biofilms were cultivated for each of the tested conditions.

Plate Counts: Cells Per Biofilm

Biofilms grown in flow cells were harvested by pumping the liquid and cells out of flow cells into sterile 1.5 mL microcentrifuge tube. The recovered cells were centrifuged at 8,000 rpm for 2 minutes. The supernatant was discarded and the resulting pellet was re-suspended in 1 mL of 50 mM KCl/NaCl solution. The suspended bacterial culture was serially diluted and plated on LB agar media. Viable cell counts were determined by enumeration of colony-forming units (CFUs) with appropriate dilutions on LB agar media after 24 hour of bacterial growth.

Live-Dead Cell Labeling

To assess cell viability of biofilms, each flow cell received 1 ml of a 1:1,000-diluted LIVE/DEAD™ Baclight™ nucleic acid stain (SYTO 9, 3.34 mM; propidium iodide, 20 mM) for 15 min, followed by rinsing with 50 mM KCl—NaCl solution for another 5 min, and then examined using Zeiss LSM 510 confocal laser scanning microscope. Argon and helium lasers were used with excitation/emission wavelengths of 480/500 nm for SYTO 9 and 490/635 nm for propidium iodide. Long-pass and dual emission filters were used for simultaneous viewing of SYTO 9 and propidium iodide stains. SYTO 9 is a green fluorescent label of nucleic acids that is permeant to cell membranes of normal cells and is thus used to label live and undamaged cells. Propidium iodide is a red-fluorescent label of nucleic acids, and since the intact cell membranes of live and undamaged cells are not normally permeant to propidium iodide, propidium iodide is commonly used to detect cells that are dead or with damaged membranes.

Figure 1:
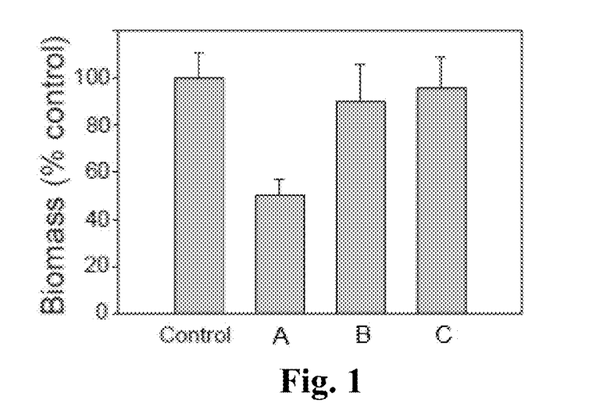
FIG. 1 depicts the synergistic effect of the components of the disclosed compositions as evidenced by the reduction in biomass (area) of P. aeruginosa biofilms versus control in flow cell assays. Graph bar A represents a composition comprising 50 μM of the disclosed antimicrobial and 30 nM hydrogen peroxide ($H_2O_2$), Graph bar B represents a composition comprising 50 μM of the disclosed antimicrobial, and Graph bar C represents a composition comprising 30 nM $H_2O_2$, versus control saline control.

FIG. 1 demonstrates the synergistic effect that the combination of the escapin intermediate products and hydrogen peroxide exhibit against *P. aeruginosa* biofilms. An example of a disclosed composition comprising 50 μM of EIP and 30 nM hydrogen peroxide (Example A) was evaluated alongside a composition comprising only 50 μM of EIP (Example B) and a composition comprising only 30 nM hydrogen peroxide (Example C). As depicted in FIG. 1, solutions representing Examples B and C resulted in marginal reductions in biomass, 10% and 4% respectively, whereas the disclosed composition resulted in at least about a 50% reduction in biomass.

Figure 2:
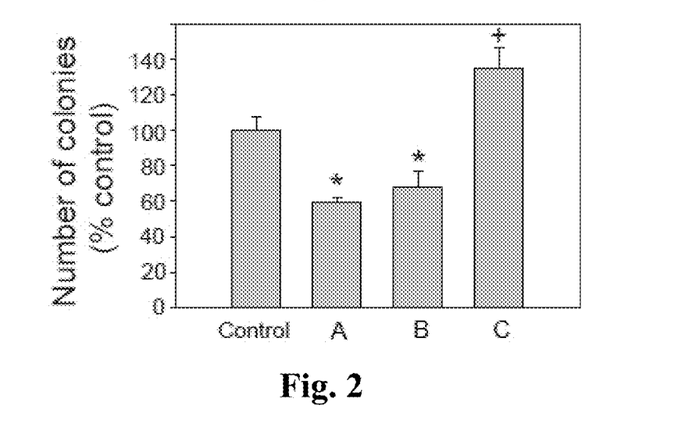
FIG. 2 depicts the number of colony forming units present as assayed from plate counts after treatment with the compositions described in FIG. 1.
Figure 3:
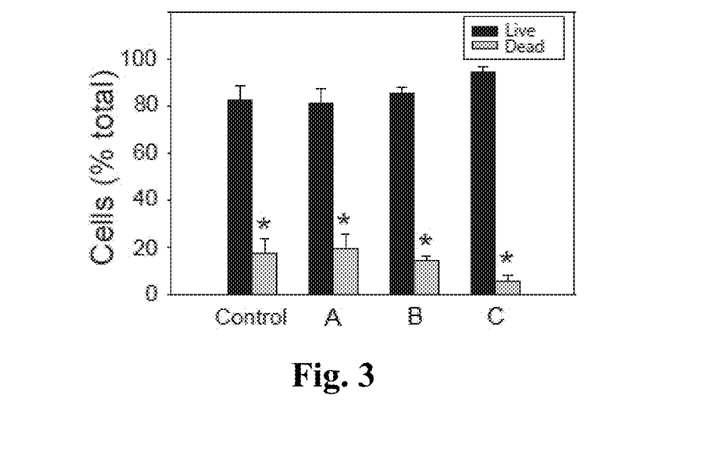
FIG. 3 depicts the relative number of live and dead cells in each sample described in FIG. 1 prior to treatment.
Figure 4A:
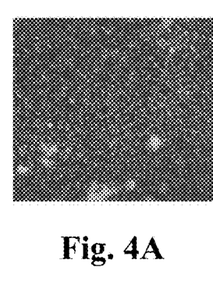
FIG. 4A to FIG. 4D are photo-micrographs of the Control sample and treated samples A to C respectively.
Figure 4B:
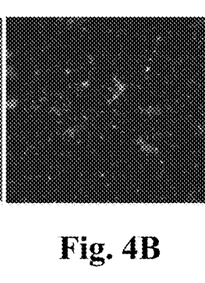
Figure 4C:
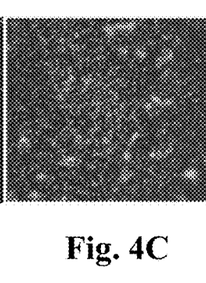
Figure 4D:
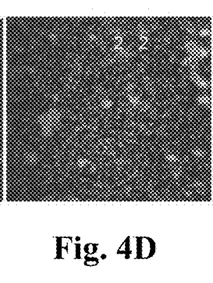

FIG. 2 depicts the number of colonies present in these Examples. For example, versus control (fixed at 100% relative value) the disclosed composition reduced the number of colonies present in the biomass by greater than 40% (Example A). FIG. 3 depicts the relative amounts of living and dead cells in the samples depicted in FIGS. 1 and 2 prior to treatment.

FIGS. 4A-4D are photomicrographs of the biofilms stained with LIVE/DEAD™ Baclight™ nucleic acid stain after treatment. The biofilms treated with the disclosed composition (FIG. 4B) when compared to saline control (FIG. 4A), a composition comprising only 50 µM of EIP (FIG. 4C) and a composition comprising only 30 nM hydrogen peroxide (FIG. 4D) had significantly less biomass (indicated by the black colored area) compared to the largely green color (indicating live/undamaged cells) with a scattering of red color (indicating dead/damaged cells) in the other treatments. Therefore, treatment of biofilms with an example of the disclosed bactericidal compositions provided greater than additive results versus EIP and $H_2O_2$ only compositions.

Figure 5:
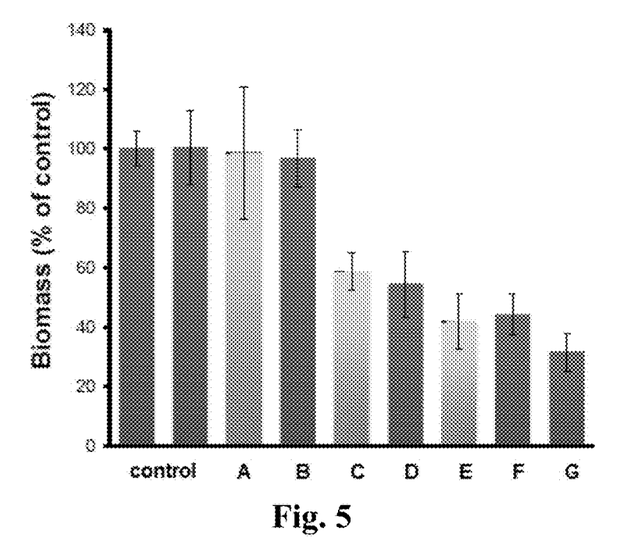
FIG. 5 depicts the reduction in biomass (area) of P. aeruginosa biofilms for compositions comprising 50 μM of the disclosed antimicrobial in combination with varying levels of $H_2O_2$ versus saline control. Graph A represents a composition 0.0003 μM $H_2O_2$, Graph B represents a composition 0.003 μM $H_2O_2$, Graph C represents a composition 0.03 μM $H_2O_2$, Graph D represents a composition 0.3 μM $H_2O_2$, Graph E represents a composition 3 μM $H_2O_2$, Graph F represents a composition 30 μM $H_2O_2$, and Graph G represents a composition 100 μM $H_2O_2$.

FIG. 5 depicts the reduction in biomass (area) of *P. aeruginosa* biofilms for compositions comprising 50 µM comprising various levels of hydrogen peroxide. As depicted in FIG. 5, even 0.0003 µM $H_2O_2$ (Example A) produces a bactericidal effect over saline control. This level of 0.0003 µM $H_2O_2$ represents an amount of $H_2O_2$ far below the levels necessary for achieving a bactericidal effect using $H_2O_2$ alone.

Histogram bar C in FIG. 5 represents a composition, comprising:
  a) about 50 µM $\Delta^1$-piperideine-2-carboxylic acid and the equilibrium products thereof;
  b) about 0.03 µM hydrogen peroxide; and
  c) the balance water.

As indicated in FIG. 5, histogram bar G represents a 70% reduction in biomass over the saline control for a composition comprising 100 µM $H_2O_2$, which is far below the typical amount of $H_2O_2$ used for sanitation. For example, a 3% solution of hydrogen peroxide which is used in medical settings for cleaning wounds has a hydrogen peroxide concentration of 1.27 M (1,270,000 µM).

What is claimed is:

1. A method for treating a *Pseudomonas aeruginosa* biofilm, comprising:
   A) admixing from about 10 µM to about 100 µM of $\Delta^1$-piperideine-2-carboxylic acid, from about 0.03 µM to about 30 µM a source of hydrogen peroxide and a liquid carrier to form an antimicrobial composition; and
   B) contacting the antimicrobial composition with a *Pseudomonas aeruginosa* biofilm.

2. The method according to claim 1, wherein the antimicrobial composition comprises from about 10 µM to about 75 µM of $\Delta^1$-piperideine-2-carboxylic acid.

3. The method according to claim 1, wherein the antimicrobial composition comprises from about 25 µM to about 75 µM of $\Delta^1$-piperideine-2-carboxylic acid.

4. The method according to claim 1, wherein the antimicrobial composition comprises from about 40 µM to about 70 µM of $\Delta^1$-piperideine-2-carboxylic acid.

5. The method according to claim 1, wherein the antimicrobial composition comprises from about 30 µM to about 60 µM of $\Delta^1$-piperideine-2-carboxylic acid.

6. The method according to claim 1, wherein the antimicrobial composition comprises from about 0.03 µM to about 3 µM of a source of hydrogen peroxide.

7. The method according to claim 1, wherein the antimicrobial composition comprises from about 0.3 µM to about 30 µM of a source of hydrogen peroxide.

8. The method according to claim 1, wherein the antimicrobial composition comprises from about 0.3 µM to about 3 µM of a source of hydrogen peroxide.

9. The method according to claim 1, wherein the pH of the antimicrobial composition is from about 5.5 to about 8.5.

10. The method according to claim 1, wherein the pH of the antimicrobial composition is from about 6.5 to about 8.5.

11. The method according to claim 1, wherein the antimicrobial composition further comprises a buffering system.

\* \* \* \* \*

UNITED STATES PATENT AND TRADEMARK OFFICE
CERTIFICATE OF CORRECTION

PATENT NO. : 9,949,925 B2  
APPLICATION NO. : 15/089365  
DATED : April 24, 2018  
INVENTOR(S) : Derby et al.

It is certified that error appears in the above-identified patent and that said Letters Patent is hereby corrected as shown below:

On the Title Page

Item (72) Inventors should read:  
Charles D. Derby, Decatur, GA (US);  
Phang C. Tai, Atlanta, GA (US);  
Eric S. Gilbert, Atlanta, GA (US);  
Marwa Nabil, Cairo, (EG)

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*